United States Patent [19]
Meyers

[11] Patent Number: 5,994,115
[45] Date of Patent: Nov. 30, 1999

[54] ARTIFICIAL SYSTEM FOR THE PRODUCTION OF INFECTIOUS HUMAN PAPILLOMAVIRUS

[75] Inventor: Craig M. Meyers, Hummelstown, Pa.

[73] Assignee: The Penn State Research Foundation, University Park, Pa.

[21] Appl. No.: 08/898,636

[22] Filed: Jul. 22, 1997

[51] Int. Cl.$^6$ .................................................. C12N 7/00
[52] U.S. Cl. ........................... 435/235.1; 435/7.1; 435/4; 435/5; 435/236; 435/239; 435/173.6
[58] Field of Search .................. 435/235.1, 7.1, 435/4, 5, 236, 239, 240.2, 240.4, 173.6

[56] References Cited

PUBLICATIONS

Frattini, et al. (1996) "In vitro synthesis of oncogenic human papillomaviruses requires episomal genomes for differentiation–dependent late expression," *Proc. Natl. Acad. Sci. USA*, 93:2062–3067.

Johnson, et al. (1993) "Growth suppression of friend virus–transformed erythroleukemia cells by p53 protein is accompanied by hemoglobin production and is sensitive to erythropoietin," *Molecular and Cellular Biology*, 13:1456–1463.

Meyers (1996) "Organotypic (raft) epithelial tissue culture system for the differentiation–dependent replication of papillomavirus," *Methods in Cell Science*, 18:201–21.

Meyers, et al. (1992) "Biosynthesis of human papillomavirus from a continuous cell line upon epithelial differentiation," *Science*, 257:971–973.

Meyers, et al. (1998) "Tissue culture techniques for the study of human papilloma viruses in stratified epithelia," *Cell Biology: A Laboratory Handbook*, (2$^{nd}$ ed.) 1:513–520.

Ozbun, et al. (1996) "Transforming growth factor $\beta 1$ induces differentiation in human papillomavirus–positive keratinocytes," *Journal of Virology*, 70:5347–5446.

Meyers, et al. (1997) "Synthesis of Infectious human papillomavirus type 18 in differentiating epithelium transfected with viral DNA," *Journal of Virology*, 71:7381–7386.

Ozbun, et al. (1997) "Characterization of late gene transcripts expressed during vegetative replication of human papillomavirus type 31b," *Journal of Virology*, 71:5161–5172.

Ozbun, et al. (1988) "Temporal usage of multiple promoters during the life cycle of human papillomavirus type 31b," *J. Virol.*, 1880–97.

*Primary Examiner*—Frank C. Eisenschenk
*Assistant Examiner*—Ali R. Salimi
*Attorney, Agent, or Firm*—Thomas J. Monahan

[57] ABSTRACT

Artificial systems for the production of infectious human papillomavirus allow development of diagnostic and therapeutic strategies based on replication and infectivity studies for diseases caused by these viruses. The artificial introduction of papillomavirus genomic DNA into an epithelial cell line. In particular, HPV type 18 genomic DNA is transfected into primary keratinocytes. Transfection is followed by clonal expansion of the transfected cells, and induction of epithelial stratification and differentiation in organotypic cultures resulting in the synthesis of virions. Virus particles synthesized were approximately 50 nanometers in diameter as observed by electron microscopy. In particular HPV18 virions produced by the system and purified by an isopycnic gradient were capable of infecting keratinocytes.

6 Claims, 7 Drawing Sheets

ARTIFICIAL SYSTEM FOR THE PRODUCTION OF INFECTIOUS HUMAN PAPILLOMAVIRUS

The government may have rights in the invention because of partial support provided by the following grants: NIH Training Grant T32 CA60395, Public Health Service fellowship National Cancer Institute CA-66316, American Cancer Society IRG-196, and National Cancer Institute CA64624.

An artificial system for the production of infectious human papillomavirus (HPV) facilitates development of diagnostic and therapeutic strategies based on replication and infectivity information for diseases caused by these viruses.

BACKGROUND OF THE INVENTION

Cancer of the cervix is the most common cancer in developing countries and the second most common in women worldwide (Parkin et al., 1993). Papillomaviruses are associated with greater than 90% of all cases of cervical cancers. Over 70 human papillomavirus (HPV) types have been identified with subsets of viruses that are predominately associated with malignant or benign neoplasias of the anogenital area, particularly the cervix (Salzman et al., 1987).

Although human papillomaviruses (HPVs) are implicated in the etiology of anogenital cancers, the complete story is not yet known. What is suspected is that expression of the HPV E6 and E7 oncoproteins may contribute to the carcinogenic process. Progressive loss of the ability to differentiate, and resistance to the growth-inhibitory effects of endogenous signals, also appear to be important in multistep tumorigenesis.

To develop therapeutic and diagnostic strategies directed toward papillomavirus caused diseases, the virus must be available for analysis. The study of the human pathogenic papillomaviruses (HPVs) and the ability to manipulate the virus for use in diagnostic assays or vaccines, has been hampered by the inability to propagate the virus in tissue culture. However, some progress has been made.

Because the replication cycle of papillomaviruses is intimately associated with the proliferation/differentiation cycles of terminally differentiating epithelium, it has been particularly difficult to cultivate and analyze various types of HPVs in vitro. Following infection of proliferating basal cells in epithelial tissues, papillomavirus replicates its genome to approximately 50 to 200 copies and maintains this copy number in basal cells during the productive life cycle of the virus. When a basal cell divides, one of the daughter cells migrates upwards and begins the process of terminal differentiation. The signal transduction and gene expression pathways that are elicited during the differentiation process regulate viral gene expression. Concomitant with the differentiation process, papillomavirus genes are expressed, viral DNA is amplified, viral late proteins are translated, and virion morphogenesis occurs. Papillomavirions are sloughed off with the squames of the outermost epidermal layer and can then infect another host. Because of this dependency on terminal epithelial differentiation for replication, papillomaviruses cannot grow in ordinary monolayer culture; this limitation has hindered studies on the papillomavirus life cycle.

The organotypic (collogen raft) tissue culture system accurately mimics an in vivo cellular environment and architecture (Ozbun and Meyers, 1996). Uses of the system are exemplified by investigations of the TGF-$\beta$1 response of HPV-positive keratinocytes derived from neoplastic cervical biopsies. For example, transforming growth factor $\beta$1 (TGF-$\beta$1) is a potent growth inhibitor for a variety of cultured cells. However, there have been conflicting reports on the ability of TGF-$\beta$1 to inhibit the growth of HPV-positive keratinocytes in monolayer cultures. Using organotypic raft cultures, some of these conflicts were elucidated (Ozburn et al., 1996).

The addition of 12-O-tetradecanoyl phorbol-13-acetate to the media of organotypic (raft) cultures increased expression of physiological markers of keratinocyte differentiation and concomitantly induced production of virions. Capsid production was detected in differentiated suprabasal cells. Virions approximately 54 nanometers in size were observed by electron microscopy in cross sections of raft tissue in the suprabasal layers. Virions purified through isopycnic gradients were found to contain type 31b DNA and exhibited an icosahedral shape similar to that of papillomaviruses found in clinical samples (Meyers et al., 1992).

The differentiation-specific amplification of episomal viral DNA, late gene expression, and virion morphogenic stages of HPV31 replication have been achieved in organotypic or (collagen raft,) cultures (Meyers et al., 1992; Frattini et al., 1996). However, culture systems continue to be deficient in the ability to propagate stocks of HPV competent for replication and infectivity studies. Additionally, investigation of the complete differentiation-dependent life cycle of HPV in vitro has been limited to a single viral type, HPV31. Another problem is the dependency on neoplastic biopsy material to derive cell lines. High risk HPV-contained cell lines established from biopsy material and primary cells transfected with a complete viral genome generally harbor HPV genomes that are integrated into the host DNA therefore are impaired in their ability to carry out a complete viral life cycle.

New methods are needed for in vitro viral propagation systems in particular for production of infectious viruses.

SUMMARY OF THE INVENTION

Infectious papillomavirus is synthesized in an artificial, in vitro system. The artificial system of infectious papillomavirus includes a dermal equivalent, cells derived from differentiating epithelium and transfected with papillomavirus DNA, a support for the transfected cells and conditions suitable for the transfected cells to produce papillomavirus. Preferred differentiating epithelial cells are keratinocytes. In an embodiment of the invention, infectious HPV18 is synthesized in differentiating epithelium transfected with the viral DNA.

A method for producing infectious papillomavirus in the artificial system includes the following steps: obtaining a dermal equivalent, contacting the surface of the dermal equivalent with cells of a cell line derived from differentiating epithelium e.g. keratinocytes, and transfected with papillomavirus HPV DNA to form a cellular composition, transferring the composition to a support; and providing a suitable environment allowing the papillomavirus to be produced. A dermal equivalent is generally constructed of a mixture of type I collagen and fibroblasts. The transfecting DNA includes a mutant DNA. Same mutant DNAs lead to production of attenuated viruses useful for making vaccines.

A method for investigating the effects of a composition, e.g. a candidate inhibitor, on HPV positive cells comprises obtaining HPV positive cells in the artificial system of the present invention, contacting the cells with the composition, and observing the subsequent growth and development of the contacted cells to determine if there is an effect of the composition based on comparisons with and without the composition.

Efficient in vitro synthesis of infectious HPV is optimized with a cell population homogenous in copy number and maintenance of episomal viral DNA. Human papillomaviruses can be propagated in vitro in quantities sufficient to investigate questions concerning the biology of the infectious process of the virus. This tissue culture system can be used to propagate any papillomavirus type if the viral DNA is available. This is particularly useful in the assessment of viral serology. That is, viral particles produced in this system can be used to test a patient's serum to determine whether there is evidence of an infection and, if so, to determine the viral types(s) involved in the infection.

Mutant papillomaviruses can also be produced using the system and methods of the present invention. Because DNA is the starting point, mutations can be introduced specifically and easily into known genes or functional regions. This mutated viral DNA can be made in large quantities and used for transfection to make more virus. Chimeras, i.e. mixture of DNA from different sources, can also be made. Mutant viruses are useful to investigate the mechanisms of the viral life cycle, virion morphogenesis, and infectivity. They can also be used to produce attenuated viruses, of particular use in making vaccines. Attenuated viruses are viruses that have been weakened by genetic manipulation, in their ability to cause disease (an example is the polio vaccine). The virus is still capable of infection but is limited in its pathogenicity. During infection the immune system mounts a response. The attenuated virus is cleared either due to it being defective and incapable of maintaining the infection, or cleared by the immune system. Boosters may be needed to increase the immunity. Defective viruses cannot grow. Aspects of the invention include the development of anti-viral therapies.

BRIEF DESCRIPTION OF THE DRAWINGS

FIG. 1 depicts examination of HPV18 DNA transfected HFK raft cultures for the presence of virus particles;

FIG. 5 shows electron micrographs of HPV18 virions approximately 50 nm in diameter. The concentration of virions produced in the subcloned line HCK 18:1Bj resulted in the clumping of the virions as seen in FIGS. 5A and B, (arrows point to representative viral particles). Bars in (A) and (B) equal 50 nm. Purified virions from subcloned cell lines were diluted 20-fold in TE buffer [pH 8.0] to prevent clumping; individual particles were observed in FIGS. 5C,E,F.

DESCRIPTION OF THE PREFERRED EMBODIMENTS

An artificial system for the production of infectious human papillomavirus (HPV) facilitates development of diagnostic and therapeutic strategies based on replication and infectivity studies for diseases caused by these viruses.

Figure 1A:
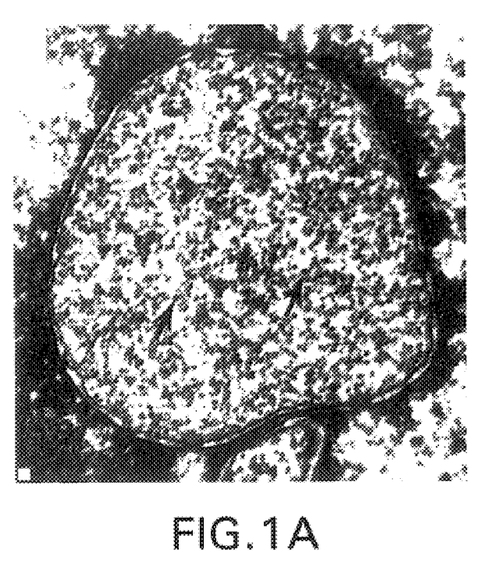
FIG. 1A shows a representative nucleus with numerous virions scattered throughout intranuclear space (arrows point to representative viral particles; bars equal 100 nm).
Figure 1B:
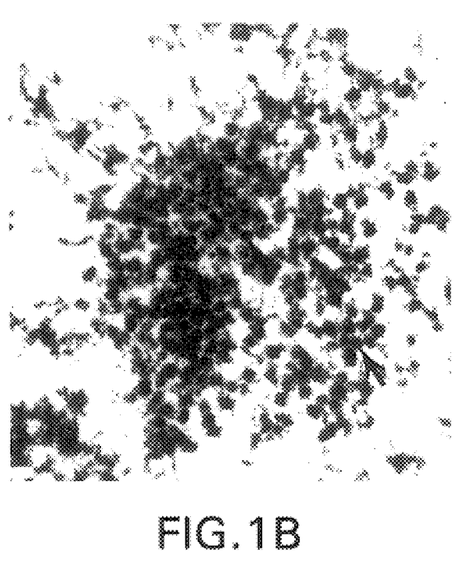
FIG. 1B is an enlargement of a second representative nucleus containing virions (arrows point to representative viral particles; bars equal 100 nm).

The invention relates production of infectious virus of a preselected HPV type by transfecting differentiating epithelial cells, e.g., human ectocervical keratinocytes (HCK) and human foreskin keratinocytes (HFK), with HPV DNA. In an embodiment, the maintenance of episomal HPV18 viral genomes in a system of the present invention was confirmed by Southern (DNA) blot hybridization. Cell lines stably maintaining episomal copies of HPV18 DNA were subsequently allowed to grow as stratified and differentiated epithelial tissues in an organotypic culture system. Electron microscopy of thin-sections of organotypic culture tissue demonstrated nuclei containing virus particles approximately 50 nm in diameter (FIG. 1). To obtain this evidence, raft culture tissue cross sections were fixed with glutaraldehyde and stained with uranyl acetate. FIG. 1A shows a representative nucleus with numerous virions scattered throughout intranuclear space (arrows point to representative viral particles). FIG. 1B is an enlargement of a second representative nucleus containing virions (arrows point to representative viral particles). Bars equal 100 nm. The presence of virus particles was limited to the upper suprabasal layers of the epithelium, and the particles observed were similar to those detected in clinical biopsy material from low-grade lesions (Shally et al., 1996). Results obtained were reproducible using several HPV18 DNA-transfected HCK and HFK lines.

1. Transfecting Cells with HPV

To prepare the artificial system, linear copies of HPV18 DNA were electroporated with a selected marker into foreskin and ectocervical primary keratinocyte cell lines. A Hygromycin B selectable marker was used, but any selectable marker is suitable i.e. G418. The DNA was prepared by standard DNA preparation protocols, then it was EtOH precipitated and resuspended and used at a concentration of 1 μg/10 μl.

Foreskin and ectocervical keratinocytes were isolated from newborn circumcision and adult hysterectomy tissue specimens, respectively. The dermis was removed from the epidermis and discarded. The epidermis was cut into approximately 2-mm square pieces (tissue "chips"), placed into a 10-cm tissue culture dish and allowed to partially dry at room temperature. Culture media was added to amply cover the tissue, and samples were incubated at 37° C. Media were changed every other day. Explants were observed daily for outgrowth of cells from the tissue chips.

After outgrowth of cells began, mitomycin C-treated J2 3T3 (Rheinwald and Green, 1975) cells were prepared and added to the explant cultures. Adding mitomycin C treated cells at this point differs from previously published techniques. This procedure maintains cells in an environment more similar to the in vivo environment, allowing them to maintain their in vivo phenotype. When outgrowths covered a third of the plate they were trypsinized and frozen for long term storage.

Bulk DNA preparations were prepared by standard techniques, then DNA was restriction digested to give linear copies of the viral DNA, thereby releasing it from the vector DNA. Viral and vector DNA were then phenol/chloroform extracted, chloroform extracted, EtOH precipitated, and resuspended in TE buffer [pH 7.6] at a concentration of 7.5 $\mu$g/ml. Viral DNA was used in a linear form and was not purified from the vector DNA. Using linear viral DNA is novel for assaying DNA types.

Cells that obtained DNA via the electroporation procedure were selected by adding between 10 and 25 $\mu$g of Hygromycin B per ml of media beginning about 48 to 72 hours after electroporation. Selection was continued until killing of the cells was observed as determined when cell formed numerous vacuoles round up and float off the plate. The amount of time of treatment with Hygromycin B is empirical based on observations that are routine.

Monolayers were passaged and frozen at different passages. Passage number does not appear to be a crucial factor as long as the viral DNA stays episomal as determined by Southern blot. However, cells passaged over twenty times are not preferred because they may begin to lose their ability to differentiate.

Cells were frozen at a concentration of 1–2×10$^6$ per ml in epithelial freezing media. Freezing media contains standard E media with twice the amount of fetal calf serum, 15% fetal calf serum, and 22% glycerol. This freezing media is known to those of skill in the art for freezing primary keratinocytes. Standard E media was used but with and without EGF (see protocol herein). Serum lots were tested for best differentiation results.

2. Confirmation of Episomal Cell Lines

The cells were analyzed at different passages by Southern blot analysis. Cells were preferably analyzed at passages 3 and 4. Many cell lines were observed that had viral DNA episomally maintained. Episomal viral DNA was observed in cell lines from passage 1 to passage 12. The parental (transfected lines) were subcloned, then analyzed by Southern blot. Virus were purified from the parental lines electroporated with HPV18 DNA, but with minimal success. Southern blots representing some of the subclones were made. Cell lines were heterogeneous as to their maintenance and copy number of HPV DNA. The parental lines were subcloned, which improved the results. Subcloning is a key factor in success of the artificial system, because the productivity varied among subclones and was generally greater than in the parental line.

At least half of the subcloned lines did not contain detectable viral DNA. Subcloned lines used for further analysis contained 100–200 copies of episomal HPV18 DNA. Two of the subclones used were designated "s" and "j".

3. Maintaining Episomal Cell Lines

Cell lines were grown for episomal maintenance on raft cultures. Raft cultures were grown for 12 days at an air-liquid interface of the cultures using standard E-media.

Changes made in the organotypic culture system used for the present invention include: (i) 2.4 $\mu$l of 10N NaOH per ml of collagen mix is added; (ii) the pH of the collagen matrix mix is increased by using collagen at a specific concentration (4 mg/ml); and using a calorimetric change from yellowish-red to light red as an indicator; (iii) the wire grids are bent so that they will allow using between 10 and 12 ml of media; this makes the grids sit at a specific height above the plastic tissue culture plate and supplies ample nutrients that may be lacking when less collagen mix is used.

4. Cell Analysis of Nuclei for Virions

Electron micrographs were taken of raft culture tissue sections grown using the HPV18 electroporated cells. Viral particles of proper size were observed within the nuclei of the tissue. Tissue was harvested, prepared, or examined as described herein.

5. Results On Subclones

To clone or subclone from a parental cell, cells were diluted so that single colonies would grow isolated from other colonies. Cloning cylinders (short, small glass cylinders) were used to select a specific colony from the plate. Although this is not a new technique, to the knowledge of the inventor it has never been used for this purpose, i.e. as a component of an artificial virus propogation system. This technique was previously used to make genetically pure cell lines.

Figure 2:
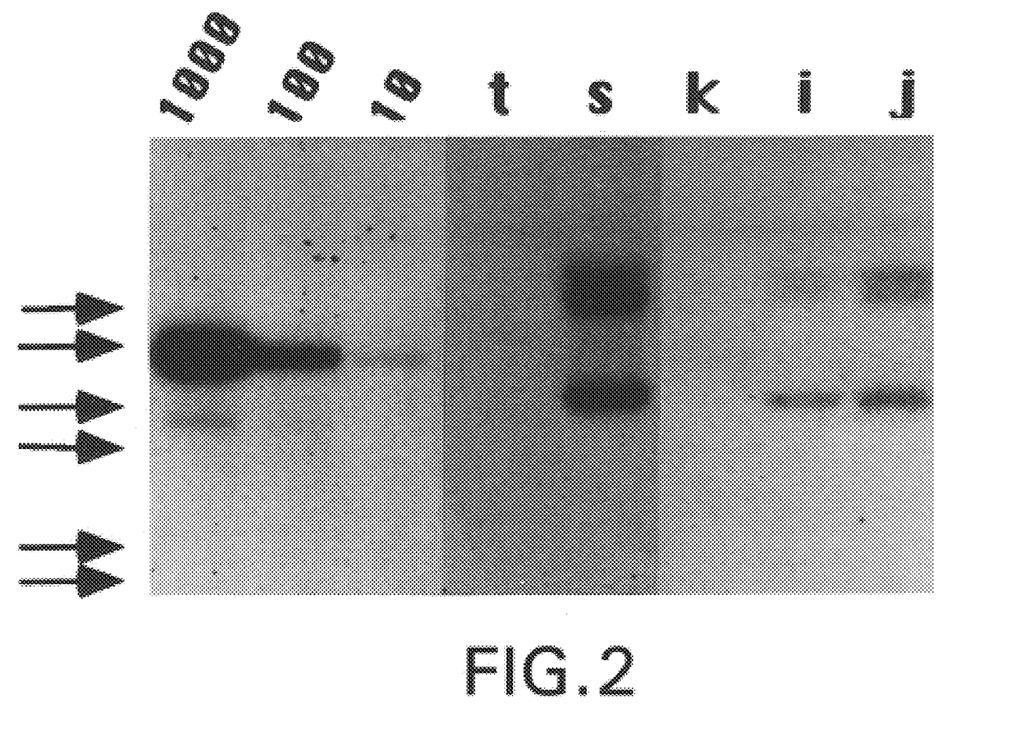
FIG. 2 illustrates Southern (DNA) blot hybridization of HPV18 DNA-transfected human ectocervical keratinocytes (HCK) subcloned cell lines.

To determine if the parental cell population was homogenous with respect to copy numbers of episomal HPV18 DNA, the parental cell lines were subcloned. A parental line that was subcloned is designated HCK 18:1B (HCK refers to "human ectocervical keratinocytes"). Southern blot hybridization analysis demonstrated that subcloned cell lines differed in their episomal HPV18 DNA copy number (FIG. 2). This result suggested that parental cell lines consisted of a heterogeneous population of cells with respect to HPV18 DNA content. Subcloned cell lines were identified alphabetically following the parental cell line designation. Results from representative subcloned lines HCK 18:1Bt, s, k, l, and j were chosen to demonstrate the heterogeneity of the parental cell lines in their copy number and maintenance of episomal viral DNA. Lanes designated 1000, 100, and 10 represent copy number controls of viral genomic DNA per 10$^6$ cells. Lanes t, s, k, l, and j, 5 $\mu$g total DNA isolated from subcloned cell lines was electrophoresed per lane in a 0.7% agarose gel. Southern blot hybridization was performed. The lowest band indicated Form I (supercoiled) viral DNA. The two upper bands indicated multimeric forms of viral DNA common to papillomavirus. Arrows on the left indicate the position of molecular size markers, that were $\lambda$ DNA HindIII digested in bp; 23,130; 9,416; 6,557; 4,361; 2,322 and 2,022.

Cesium chloride gradients of virions were prepared from the raft cultured tissues. Gradients were used to purify the virions. Using the subcloned lines, the protocols for purification included conditions for fractionating the gradient, removing specific volumes from one end of the gradient. Hoefer Scientific gradient tube fractionator (FS101), capable of fractioning 0.5 ml samples was used. Southern blot analysis of fractions from the gradient were analyzed by the standard Southern blot technique. 3 to 5×10$^9$ particles were purified. Fractions shown to be positive for viral DNA were dialyzed against multiple changes of TE buffer (pH 7.6).

Figure 3:
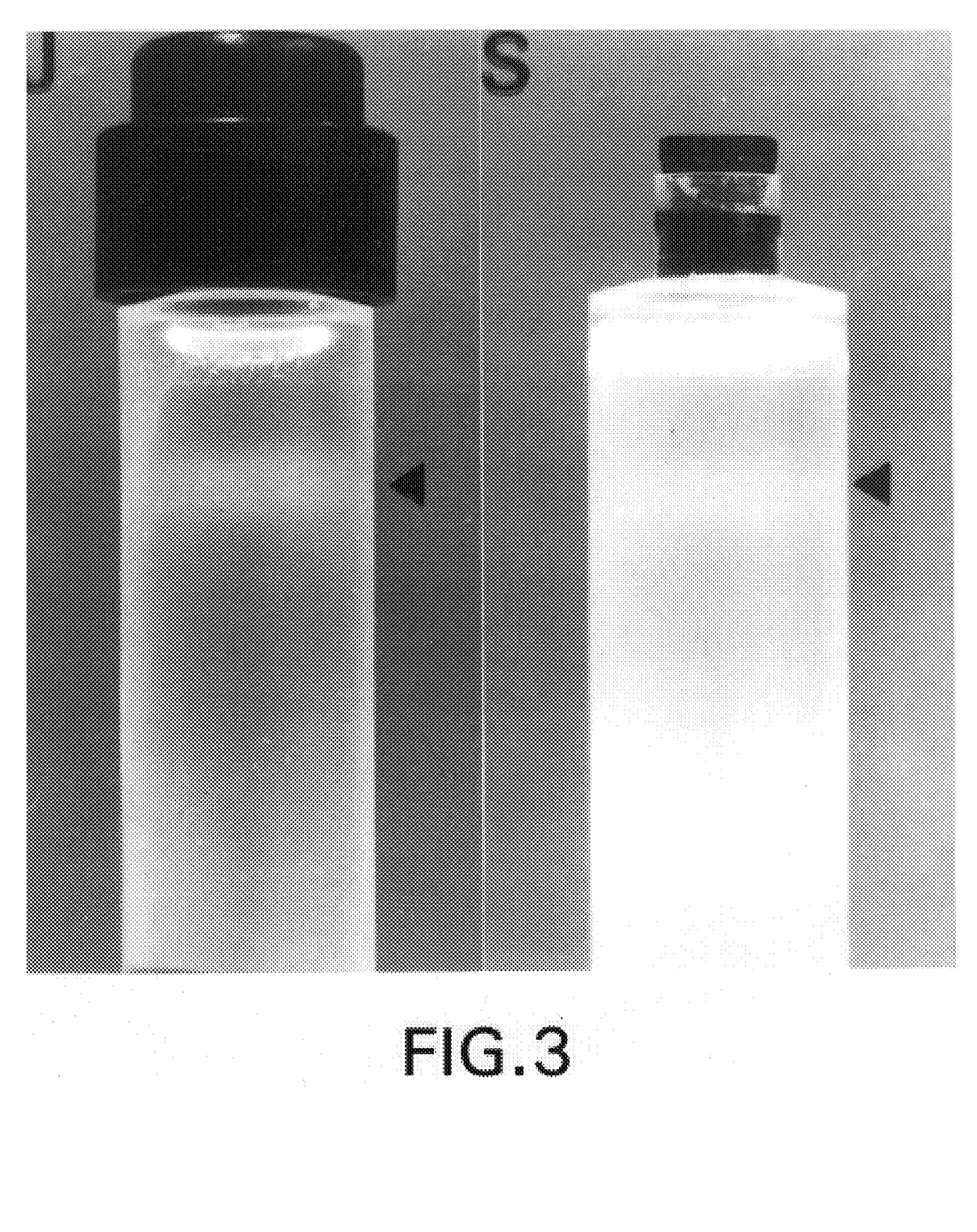
FIG. 3 shows HPV18 virions banded on isopycnic gradients. HPV18 DNA-transfected subcloned lines HCK 18:1Bj and HCK 18:1Bs raft cultures are used as representative examples.

Virus was purified from the parental and subcloned cell lines. With cell extracts from parental cell lines, it was difficult to visualize a band corresponding to the density expected for virus particles on an isopycnic gradient. However, the subcloned lines formed readily observable bands at the expected density following isopycnic gradient centrifugation (FIG. 3). Bands were visualized under normal ambient lighting. Arrows indicate bands of HPV18 virions (corresponding to 1.3 to 1.4 g/cm³). Virions were isolated by first scraping the raft culture epithelium off the collagen rafts with a scalpel and washing the tissue with 0.15 M NaCl. Tissue was ground in a mortar with sea sand, resuspended in buffer #1 (1 M NaCl, 0.05 MNa$_2$HPO$_4$ [pH 7.4]), and centrifuged for 10 min at 8,000 g. The supernatant was removed and saved on ice; the pellet was reextracted with buffer #1, and centrifuged for 10 min at 8,000 g. Supernatants were pooled, CsCl was added to a final concentration of 1.3 g/ml, and centrifuged for 24 hours at 135,000 g. Arrows indicate bands of HPV18 virions (between 1.3 to 1.4 g/cm³) observed in two typical examples.

Figure 4:
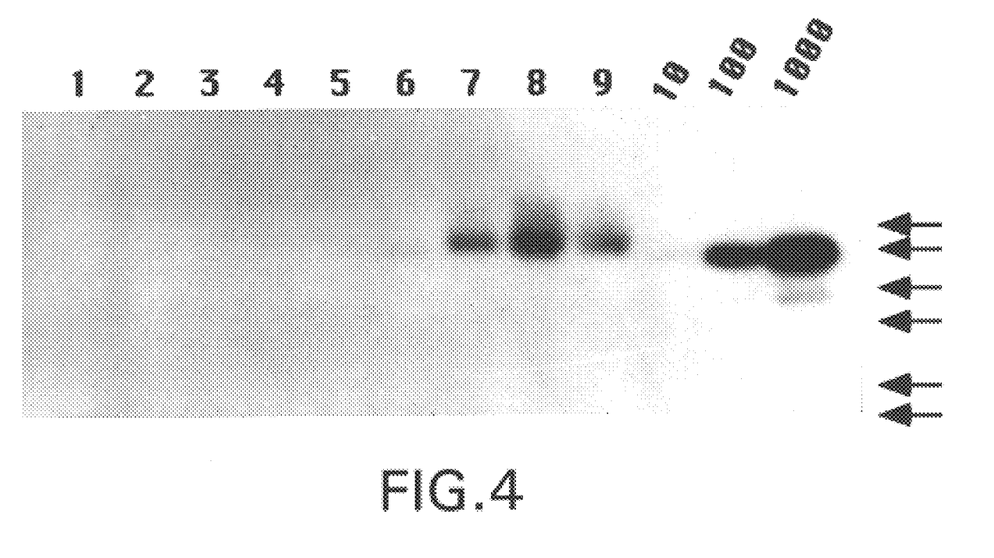
FIG. 4 illustrates Southern blot hybridization of fractions collected from virus preparations of HPV18 DNA-transfected subcloned line HCK 18:1Bs raft cultures.

Gradient fractions were analyzed by Southern blot hybridization to confirm the presence of HPV18 DNA (FIG. 4). Lanes 1 through 9 show a series of fractions, with lane 1 representing the bottom of the gradient and viral DNA appearing in lanes 7, 8, and 9. Arrows on the right indicate the position of molecular size markers, that were λ DNA HindIII digested as in FIG. 2.

Figure 5A:
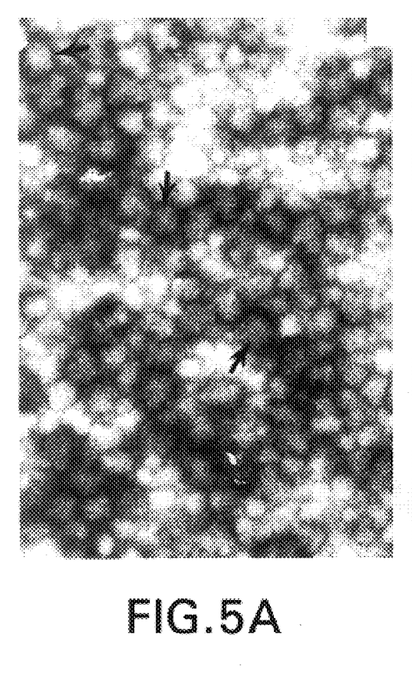
Figure 5B:
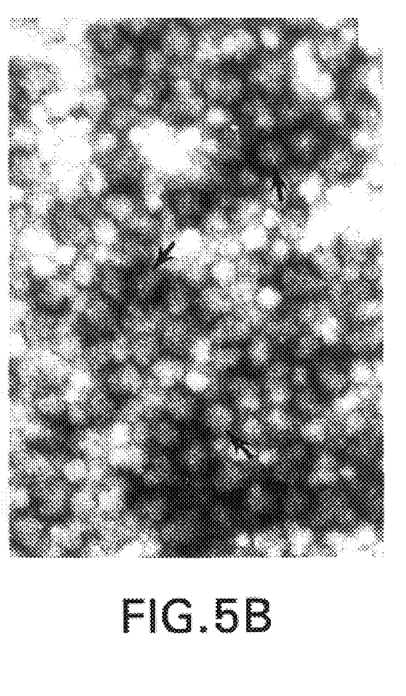
Figure 5C:
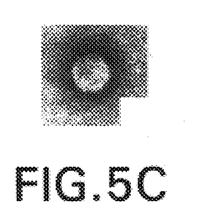
FIG. 5C shows results in subclone line HCK 18:1Bj.
Figure 5D:
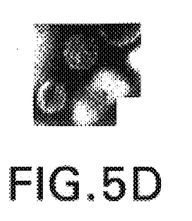
FIG. 5D shows results in parental line HCK 18:1B (undiluted preparation).
Figure 5E:
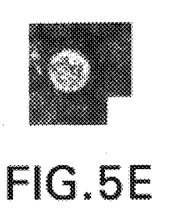
FIGS. 5E–F shows results in subclone line HCK 18:1Bs. The magnification in FIG. 5F is approximately 2× that of FIGS. 5C–E. All virus particles are approximately 50 nm in diameter.
Figure 5F:
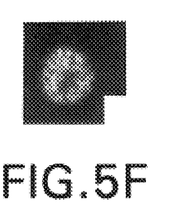

Virions were purified by CsCl isopycnic gradients as described in FIG. 3. Fractions of 0.5 ml each were collected from the gradient and dialyzed against TE buffer [pH 8.0]. DNA was purified from each fraction, and Southern blot hybridization was performed. Fractions 7, 8, and 9 of FIG. 4 were found to contain HPV18 DNA at high levels. Fractions positive for HPV18 DNA correlated to fractions where the banded virus was visually observed in the gradient (FIGS. 3,4). HPV18-DNA positive fractions contained virus particles as detected by electron microscopy (FIG. 5). Gradient fractions determined to be positive for HPV18 DNA by Southern blot hybridization were stained with phosphotungstic acid and examined by electron microscopy. The concentration of virions produced in the subclone line HCK 18:1Bj resulted in the clumping of the virions as seen in FIGS. 5A and B, (arrows point to representative viral particles). Bars in (A) and (B) equal 50 nm. Purified virions from subcloned cell lines were diluted 20-fold in TE buffer [pH 8.0] to prevent clumping; individual particles were observed (C,E,F). (C) from subclone line HCK 18:1Bj; (D) from parental line HCK 18:1B (undiluted preparation); (E–F) from subclone line HCK 18:1Bs. The magnification in (F) is approximately 2× that of (C–E). All virus particles are approximately 50 nm in diameter. The co-sedimentation of both HPV18 DNA and viral particles within the same fractions suggested that these were complete HPV18 virions. As demonstrated by electron microscopy, both parental (FIG. 5D) and subcloned cell lines (FIGS. 5A–C,E,F) were able to support the replication HPV18 virions, albeit in vastly different quantities. The levels of virions produced in the subcloned lines resulted in the clumping of the virions (FIGS. 5A–B) as has been seen with higher concentrations of cottontail rabbit papillomavirus and bovine papillomavirus purified from infected tissues. To obtain photographs of individual HPV18 virions, virus particles from subcloned cell lines were diluted (FIGS. 5C,E–F).

6. Infectivity of Viruses

Electron micrographs of HPV18 virions showed large amounts of HPV18. Purified virus was infectious as determined by using primary keratinocyte lines. (The parental line-derived virus were infectious, but fewer virions were produced.)

Standard primary human foreskin keratinocyte lines were prepared and maintained as described herein. Confluent 10 cm plates of cells were used. Samples of the virus were placed on the cells. Media was removed from the plates. Then, 50, 100, or 200 μl of viral stocks were added to 0.5 ml of culture media and this composition was added to the plates. Plates were incubated with the viral solutions for about 2 hours and were rocked (tilted plates back and forth by hand) every 15 minutes. Then 10 ml of culture media was added to each plate and plates were incubated for varying times before harvesting the RNA.

The purified HPV18 virions were capable of infection, the final step in the viral life cycle in vitro. Aliquots of HPV18 stocks were allowed to attach and infect monolayer cultures of HFK. Gradient fractions 7, 8, and 9 shown by Southern (DNA) blot hybridization analysis and electron microscopy to contain HPV 18 virions were pooled. Virions isolated from the parental cell line HCK 18:1B and two subclones derived from this parental line, HCK 18:1Bj and HCK 18:1Bs, were used. Growth media were removed from subconfluent plates of normal HFK cultures and an inoculum of 50, 100, or 200 μl of growth media was applied. Mock-infected plates were also prepared. Plates were rocked (tilting back and forth by hand) every 15 min. for 2 hours then growth media was added. The cells were incubated for 24 or 72 hours, or continuous passages post-infection at 37° C., then total RNA was extracted and analyzed for HPV18-specific spliced transcripts. Duplicate plates were also maintained by passaging infected cell lines. Data from Southern blot hybridization analysis indicate that viral inocula contained between 1–2×10⁹ particles per ml for the subclonal cell lines HCK 18:1Bj and HCK 18:1Bs, and greater than one order of magnitude fewer particles for the parental line HCK 18:1B.

Figure 6A:
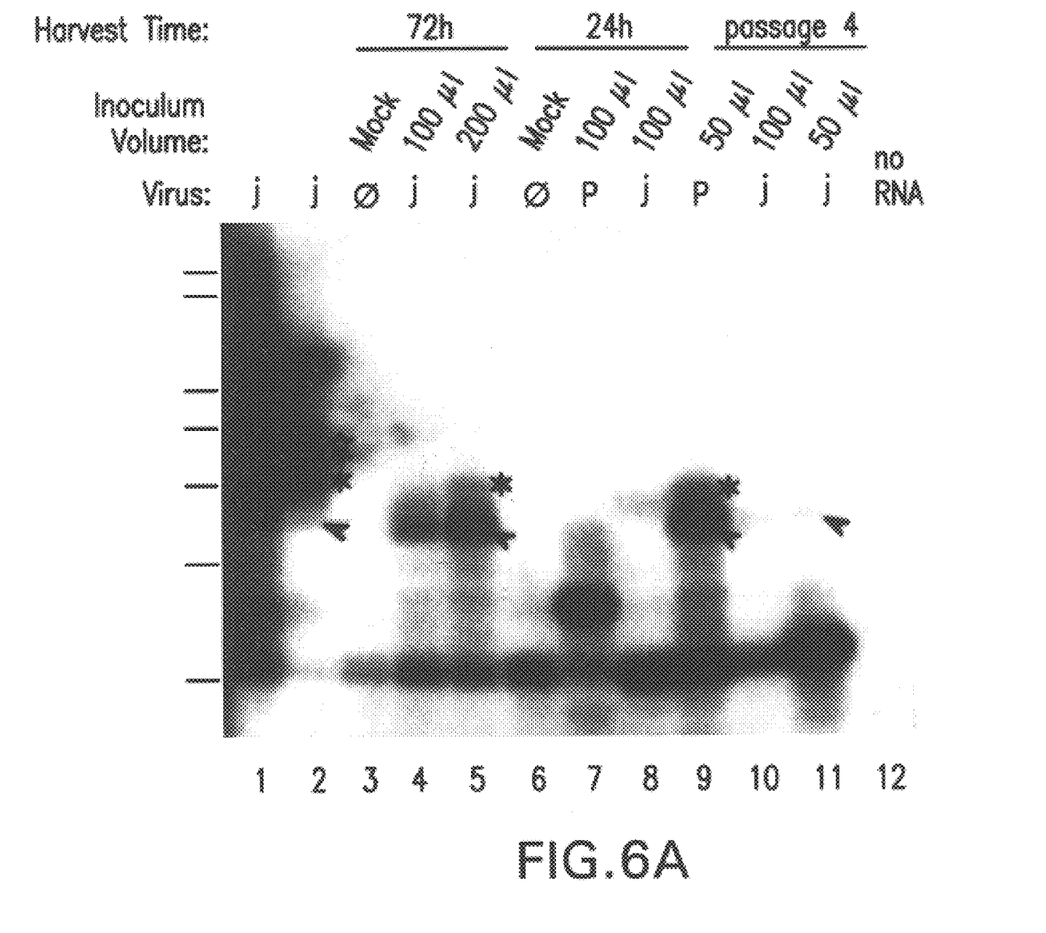
FIG. 6 illustrates identification of HPV18 specific spliced transcripts (RNA) in HPV18 infected keratinocytes. Placement and orientation are illustrated by open arrows. HPV18-specific spliced transcripts identified in the HCK 18:1Bj cell line and in the infected keratinocytes are labeled ☆, ✱, ▶, ✚, and ◆.
Figure 6B:
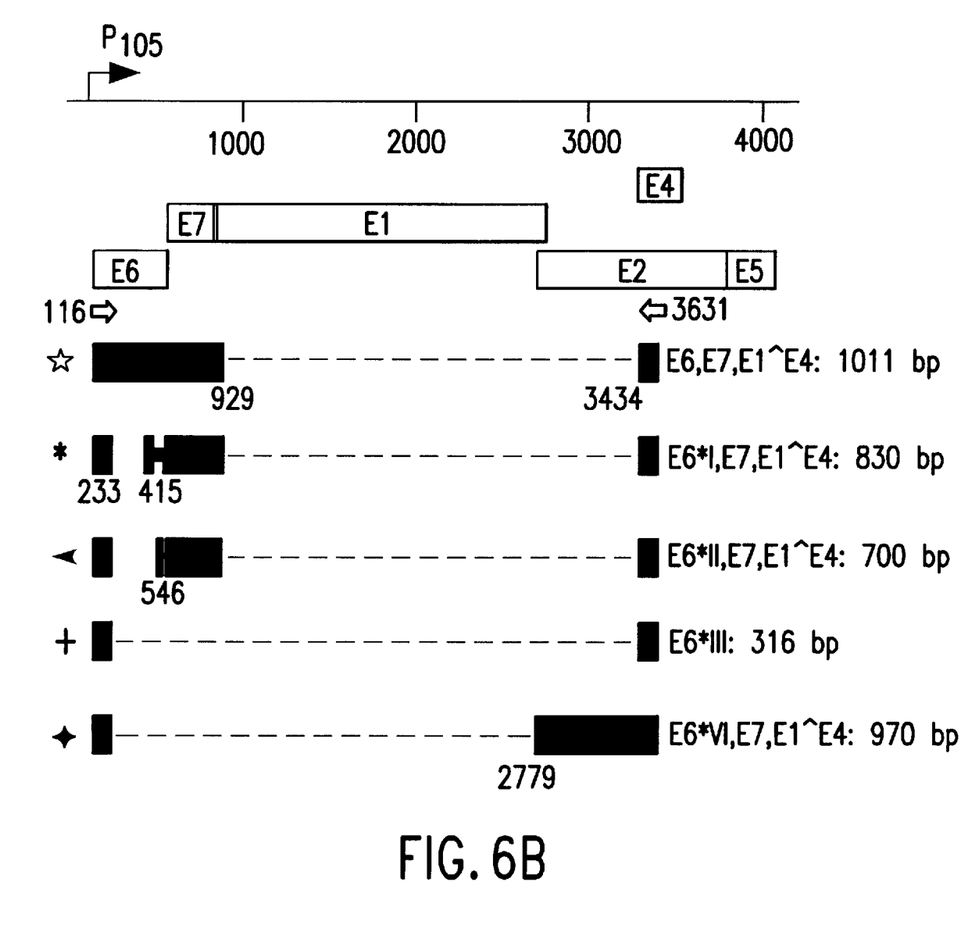

Due to the lack of an infectious assay for HPVs, the expression of viral spliced transcripts was assayed in infected cells. RNA was isolated from HPV18-infected and mock-infected HFK monolayer cultures (FIG. 6). Total RNA was extracted from HPV18-infected and mock-infected normal keratinocytes. RNA was DNase I-treated and subjected to reverse transcription. HPV18 cDNAs were PCR-amplified using primers to an E6 nucleotide sequence (5'-TGAGGATCCMCACGGCGACC-3') and to an E4/E2 nucleotide sequence (5'-GGTGTAGCTGCACCGAGAAGTGG-3'); placement and orientation are illustrated by open arrows. The cDNA products were electrophoresed in an 1.2% agarose gel followed by Southern blot hybridization. RT-PCR-amplified cDNAs from the HCK 18:1Bj subclone were cloned. Sequencing revealed cDNAs corresponding to the HPV18 transcripts E6*I,E7,E1^E4 and E6*III. The splice sites for HPV 18 transcripts E6*II,E7,E1^E4 were based on structures defined for HPV16 (12,13). (A) Southern blot of RT-PCR products. Lane 1, contains 3 μl of the PCR reaction from HCK 18:1Bj cell line cDNA; lane 2 contains 0.3 μl of each PCR reaction from HCK 18:1Bj cell line cDNA; lanes 3–12 contain 30 μl of each PCR sample. Lanes 3 to 5, normal keratinocytes 72 hour post-infection; lanes 6 to 8, normal keratinocytes 24 hours post-infection; lanes 9 to 11, normal keratinocytes 4 passages post-infection; lane 12, control, no RNA added to RT-PCR reaction. Lanes 3 and 6, mock-infections; lanes 4, 8, and 10 infected with a 100 μl inoculum of HCK 18:1Bj viral stock; lane 5, infected with a 200 μl inoculum of HCK 18:1Bj viral stock; lane 7, infected with a 100 μl inoculum of HCK 18:1B viral stock; lane 11, infected with a 50 μl inoculum of HCK 18:1Bj viral stock (B) The splicing pattern of HPV18 E6* transcripts are indicated schematically and the corresponding HPV18 nucleotide numbers of the splice sites are given. P$_{105}$ is the major early promoter of HPV18. HPV18-specific spliced transcripts identified in the HCK 18:1Bj cell line and in the infected keratinocytes are labeled ☆, *, ➤, +, and ◆.

Little is known concerning the character of HPV18 specific mRNAs. Using as a model multiply-spliced E6 transcripts (labeled E6*I, II, III, and IV) identified for HPV-16 (Shally et al., 1996), the assays were directed to similarly spliced transcripts in the HPV18-infected cells. HPV18-specific E6* spliced transcripts were demonstrated by RT-PCR in the HPV18transfected lines and in HPV18-infected HFK, but not in mock infected cells (FIG. 6). The splice donor and splice acceptor sites for HPV18 E6* and E1^E4 were previously reported and are in agreement (Johnson et al., 1993). Two E6* spliced transcripts were previously observed in HPV18 associated cervical cancer derived cell lines, but were not sequenced or otherwise characterized (Schneider-Gödiske and Schwartz, 1986).

The life-span of HPV18-infected cell lines was assessed using separate viral preparations from the subcloned lines HCK 18:1Bj, HCK 18:1Bs and the parental HCK 18:1B. Six of6 infected lines were able to grow a month longer in culture compared to the mock-infected and the normal keratinocyte cell lines. The expanded life-span lines also expressed HPV18 spliced transcripts (FIG. 6).

MATERIALS AND METHODS

Transfection

HPV18 DNA was linearized at nucleotide 2440 by restriction digest with EcoRI interrupting the E1 open reading frame. Replication and episomal maintenance was dependent on precise recircularization of the viral DNA. Viral DNA was electroporated into primary human foreskin keratinocytes (HFK) or primary human ectocervical keratinocytes (HCK).

Organotypic Raft Cultures

An in vitro organotypic (raft) culture system capable of reproducing the differentiation-dependent replication cycle of human papillomavirus is an aspect of the invention. As developed previously using neoplastic biopsy derived cell lines, a dermal equivalent is made from a mixture of type I collagen and fibroblasts. Cells of a line derived from differentiating epithelial cells such as a cervical intraepithelial neoplasia type 1 (CIN-1) are placed on top of the dermal equivalent and, while submerged, are allowed to grow to confluence. The dermal equivalent with epithelial cells on top is then lifted onto a wire grid where it remains at an air-liquid interface. From this point on the epithelial cells never come in contact with the culture media. Feeding of the epithelial cells is done by diffusion through the dermal equivalent similar to the in vitro situation. The epithelial cells under these conditions will stratify and differentiate over approximately a two week period. In an application of the culturing when an inducer of protein kinase C is added to the media, the CIN-1 derived cell lines, which maintain episomal copies of a high risk human papillomavirus will biosynthesize virion. This procedure provides information for the analysis of the interaction of human papillomavirus with its host tissue, squamous epithelium. (See Description of the Preferred Embodiment for variations used in the present invention and Meyers, 1996.)

Protocol for Purifying Virion Particles by Gradients

Cells are washed with 0.15 M NaCl and ground in mortar with regular sand;

the results of grinding are resuspended in about 25 ml of 1M NaCl; 0.05M Na Phosphate Buffer at pH 8;

the suspension is centrifuged using a ss34 rotor at 10–10.5 k rpm (8 k×g) for 10 min at 4° C.; the supernatant is saved;

the pellet is reextracted in 25 ml 1M NaCl; 0.05 MNa Phosphate Buffer at pH 8;

the suspension is centrifuged using a ss34 rotor at 10–10.5 k rpm for 10 min at 4° C.;

the supernatants are pooled;

to pellet virus, pooled supernatants are centrifuged (130 k×g) 43 k×rpm using a type 60 Ti rotor for 60 min at 4° C.; or a SW41 rotor at 33 k×rpm for 60 min at 4° C.;

the pellet is resuspended in 2.0 ml 0.05M NaCl, 0.1M EDTA; 0.05M Na Phosphate Buffer at pH 7.4;

and centrifuged using a ss34 rotor at 10–10.5 k rpm for 10 min at 4° C.; the supernatant is saved;

the pellet is reextracted in 2 ml 0.05M NaCl, 0.1M EDTA; 0.05M Na Phosphate Buffer at pH 7.4;

and centrifuged using a ss34 rotor at 10–10.5 k rpm 10 min 4° C.; the supernatants were pooled;

CsCl is added to 1.3 g/ml to the pooled supernatants;

and centrifuged at 135 k×g 39 k×rpm, using a VTi 65 rotor, 24 hr at 4° C.

Southern Blotting & Hybridization

Materials:

0.25 N HCl (20.7 ml of 12.1 N per 1 liter)

0.4 N NaOH (40.0 ml of 10 N per 1 liter)

3 sheets of 3 MM paper to be used as wicks 11 sheets of 3 MM paper to be used between membrane and paper towels GeneScreen Plus 5 mg/ml sonicated (or sheared), denatured salmon sperm (or calf thymus) DNA Methods:

AGAROSE GEL ELECTROPHORESIS AND SOUTHERN TRANSFER

1. Photograph gel and measure distance of DNA markers. Cut away excess gel.

2. Soak gel in 2 volumes of 0.25M M HCl with gentle shaking until bromophenol blue changes color (~5–15 min).

3. Rinse gel 5 min in dH$_2$O with gentle shaking.

4. Prewet nylon membrane in H$_2$O. Soak in 0.4 M NaOH for at least 20 minutes while gel is soaking in NaOH.

5. Wet 3 MM paper in 0.4 N NaOH and lay over glass plate in a container (smooth down with pipette).

6. Transfer gel, flipping it upside down onto the smoothed wicks (smooth down with pipette).

7. Place nylon membrane (GENESCREEN PLUS) atop gel (smooth down with pipette).

8. Place one sheet of 0.4 N NaOH soaked 3 MM paper that is slightly larger than the membrane atop the membrane (smooth down with pipette).

9. Place ten sheets of dry 3 MM paper slightly larger than the membrane on top of wetted 3 MM.

10. Stack paper towels 6–8 inches high on top 3 MM paper.

11. Place glass plate and weight on top.

12. Add 0.4 N NaOH, transfer buffer into container. Transfer overnight, but be certain transfer buffer does not dry up.

13. Following transfer, remove membrane and mark positions well with a pencil.

14. Rinse membrane with 2×SSC. Use gloved hands to carefully wipe membrane to remove possible gel remains.

15. Place membrane on sheet of 3 MM paper to air dry for approximately 30 min.

16. Place membrane into an envelope of 3 MM paper, close (staple) and bake in vacuum oven at 80° C. for 2 h.

17. Remove membrane and wet in 2× SSC just prior to prehybridization.

Prehybridization and Hybridization, Use 50 μL/cm² of Membrane

| Constituent (final conc.) | 30 ml prehyb | 33 ml hyb | Probe |
|---|---|---|---|
| Formamide (50%) | 15.0 ml | 15.0 ml | ___ μl DNA (25–100 ng) |
| 20× SSPE (4×) | 6.0 ml | 6.0 ml | ___ μl dH$_2$O |
| 100× Denhardts (5×) | 1.5 ml | 1.5 ml | 5.0 μl $^{32}$P-dCTP |
| 20% SDS (1%) | 1.5 ml | 1.5 ml | 3.0 μl dA, G, TTP mix |
| Dextran sulfate (10%) | — | 3.0 gm/ 4.2 ml dH$_2$O) = 6 ml | 2.0 μl 10× Soln. #6 |
| 5 mg/ml ssDNA (.5 mg/ml) | 3 ml | 3 ml | 1.0 μl Klenow |
| dH2O | 3 ml | — | 20.0 μl TOTAL |

1. Prehybridize in a 42°–45° C. waterbath for 1–2 hr to O/N.

2. Remove prehybridization mix.

3. Prepare probe by calculating the amount of probe needed (10$^6$ cpm/ml of hybridization mix): 5 μl probe DNA; denature 10 min at 100° C., place immediately on ice, add all other compounds and incubate 30 min at 37° C. Stop reaction by adding 2 μl of 500 mM EDTA. Adjust volume to 100 μl and spin for 5 min in a Quick Spin Column. Count 2 μl. Add 50 μl of 10 mg/ml denatured at 100° C. ssDNA.

4. Add an equal volume of 100% formamide to probe and denature at 95–100° C. for 10 min.

5. Cool probe on ice for 15 min.

6. Add hybridization mix to membrane and then immediately add the probe, seal and incubate in a 42° C. waterbath for 12–16 h.

7. Wash blot: rinse in 2× SCC, 0.1% SDS RT.

1×, 15 min RT in 2× SSC, 0.1% SDS vigorously shaking
1×, 15 min RT in 0.5× SSC, 0.1% SDS vigorously shaking
1×, 15 min RT in 0.1× SSC, 0.1% SDS vigorously shaking
1×, 30 min 50° in 0.1× SSC, 0.1% SDS vigorously shaking 8. Blot on filter paper, air dry, wrap with saran wrap and expose.

Note: Same amounts are blank because they are determined for each experiment by methods known to those of skill in the art.

Keratinocyte Electroporation Protocol

1. The day before the electroporation set up feeder plates (three plates per electroporation).

2. Digest the DNA of choice, phenol/chloroform extract, chloroform extract, EtOH precipitation, and resuspend in _λTE (~7.5 μg/10λ).

(if drug selection is required, prepare the appropriate DNA (such as pSV$_2$neo or PSV$_2$ Hygro) at 1 μg/10λ.)

3. Prepare salmon sperm DNA (denatured/sonicated) 10 mg/ml. Boil for at least 5 min before using. Place on ice immediately after boiling.

4. Aliquot into 1.5 ml Eppendorf tubes:

10λ of the DNA of choice (7.5 μg)

10λ of the selection marker (1 μg) if needed 4.25λ of salmon sperm DNA (42.5 μg) into one tube per each electroporation.

5. Trypsinize and count the keratinocytes.

$$\underline{\phantom{xxxx}} \text{ cells} = \underline{\phantom{xxxx}} \text{ ml of E} +$$

10% fcs with 5 mM BES at pH 7.2 (from a 500 mM BES stock)

$$20 \times 10^6 \text{ cells/ml}$$

6. Mix 250λ cells (5×10$^6$ cells) with the DNA mix.

7. Incubate at room temperature for 10 minutes.

8. Transfer to a cuvette.

9. Electroporate 210 μg 960 μFd (time constant≅40)

10. Incubate at room temperature for 10 minutes.

11. Layer each electroporation onto 10 ml of E+10% fcs (fetal calf serum) and centrifuge ~300 rpm for 10 minutes.

12. Resuspend each electroporation in 6 ml of E+10% fcs.

13. Place 2 ml of the electroporated cell solution onto each of the three feeder plates prepared the day before. (refeed the feeder plates before adding the electroporated cells).

14. Next day add EGF (Epidermal Growth Factor) to each plate to a 5 ng/ml concentration from the 200× stock tube. Wait two to three days before selection.

DOCUMENTS CITED

Frattini, G., Lim, H. B., Laimins, L. A., *Proc. Natl. Acad. Sci. U.S.A.* 92:3062 (1996).

Johnson et al., *Mol. Cell Biol,* 13:1456 (1993).

Meyers, *Methods in Cell Science,* 18:201–210 (1996).

Meyers, M. G. Frattini, J. B. Hudson, L. A. Laimins, *Science* 257:971 (1992).

Ozbun, M. A. and Meyers, C., *J. Virol,* 70(8):5437–5446 (1996).

Parkin, D. M., P. Pisani, and J. Ferlay, *Int. J. Cancer,* 54:594–606 (1993).

Rheinwald, J. J. and Green, H. (1975) *Cell* 6:331–343.

Salzman, P. and Howley, P. M., Eds., *The Papillomaviruses,* vol. 2 of *The Papovaviridae* (Plenum, New York, 1987).

Schneider-Gädicke and E. Schwarz, *EMBO J.* 5:2285 (1986).

Shally et al., *Virus Res.* 42:81 (1996).

I claim:

1. A method for producing infectious papillomavirus, said method comprising:
   a. obtaining a dermal equivalent, wherein the dermal equivalent comprises type I collagen and fibroblasts;
   b. contacting the dermal equivalent with cells of a differentiating epithelial cell line transfected with papillomavirus DNA to form a cellular composition;
   c. transferring the composition to a support; and
   d. providing conditions that produce papillomavirus.

2. The method of claim 1, wherein the differentiating epithelial cell line is a keratinocyte cell line.

3. The method of claim 1, wherein the cells are transfected with a mutant DNA.

4. The method of claim 3, wherein the mutant DNA, when expressed, produces on attenuated or defective virus.

5. The method of claim 1, wherein the papillomavirus is a human papillomavirus.

6. A method for producing papillomavirus for use in the performance of serological assays, said method comprising:
   a. obtaining a dermal equivalent, wherein the dermal equivalent comprises type I collagen and fibroblasts;
   b. contacting the dermal equivalent with epithelial cells transfected with papillomavirus of a specific serological type to form a composition;
   c. transferring the composition to a support; and
   d. providing conditions that produce papillomavirus.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: primer

<400> SEQUENCE: 1
tgaggatcca acacggcgac c                                                    21

<210> SEQ ID NO 2
<211> LENGTH: 23
<212> TYPE: DNA
<213> ORGANISM: primer

<400> SEQUENCE: 2
ggtgtagctg caccgagaag tgg                                                  23